United States Patent [19]
Moran

[11] 3,991,414
[45] Nov. 9, 1976

[54] HEALTH CARE SIGNALING DEVICE

[76] Inventor: Jack L. Moran, Box 53, Spearman, Tex. 79081

[22] Filed: Aug. 2, 1971

[21] Appl. No.: 168,051

[52] U.S. Cl. .............................. 340/272; 340/279
[51] Int. Cl.² ....................................... G08B 13/10
[58] Field of Search ................... 340/272, 278, 279

[56] References Cited
UNITED STATES PATENTS

| | | | |
|---|---|---|---|
| 1,969,554 | 8/1934 | Gloudemans | 340/272 |
| 2,436,518 | 2/1948 | Lieffers | 340/279 |
| 3,325,799 | 6/1967 | Farres | 340/278 |

Primary Examiner—Thomas B. Habecker
Attorney, Agent, or Firm—Harold H. Flanders

[57] ABSTRACT

A signaling device for health care to indicate when the occupant of a bed is restless or out of bed incorporated into and operating in response to a specially designed array including at least two deflection elements having a crossed, "X" configuration and a control detection device transverse to the bed, the array being under the spring structure of the bed and operatively connected thereto for activating detection and circuit completing apparatus responsive to detect the deflections produced by movements of the occupant of the bed and producing a signal indicative of the movement on or from the bed.

8 Claims, 8 Drawing Figures

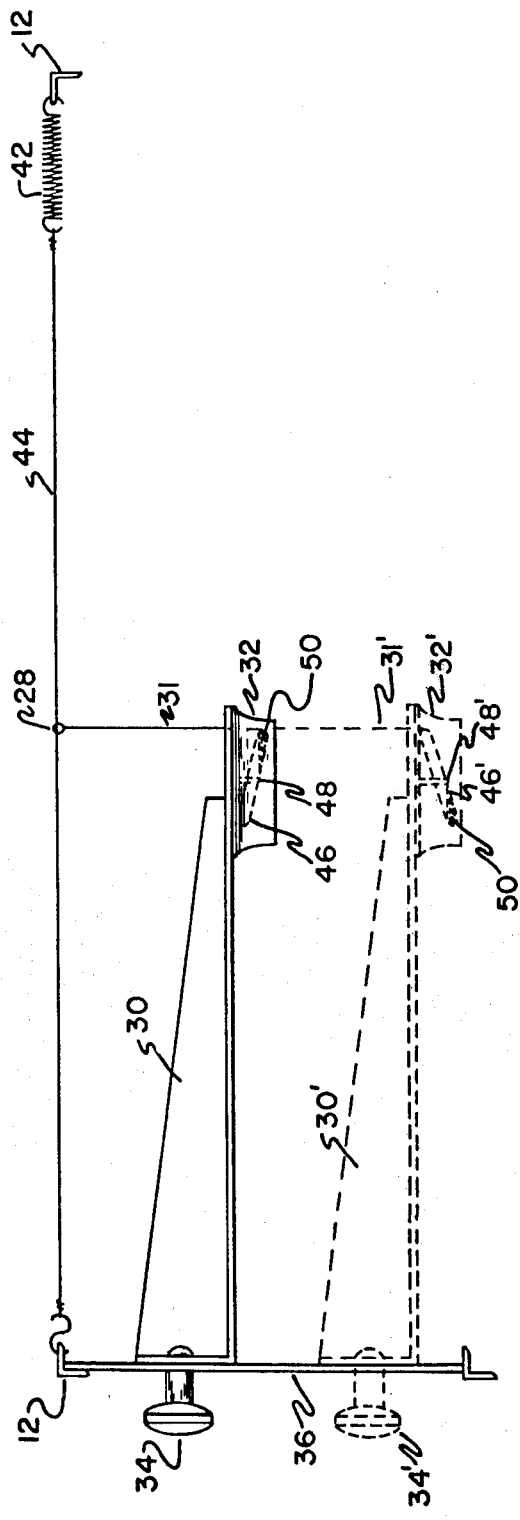
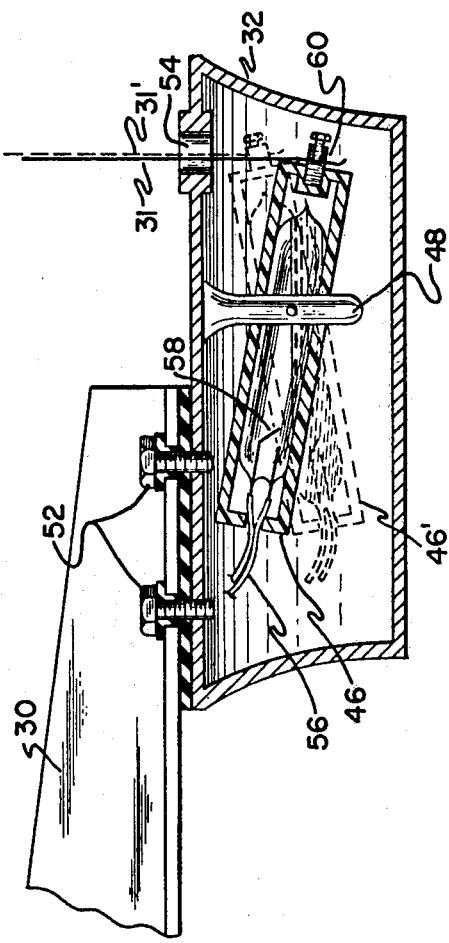

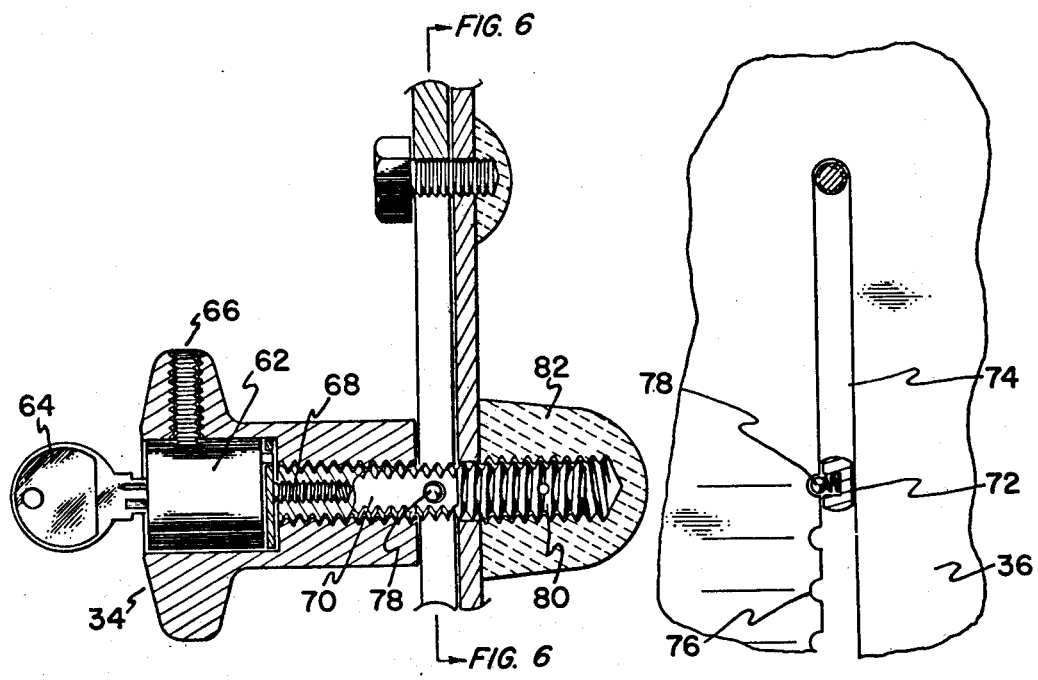
FIG. 5
FIG. 6
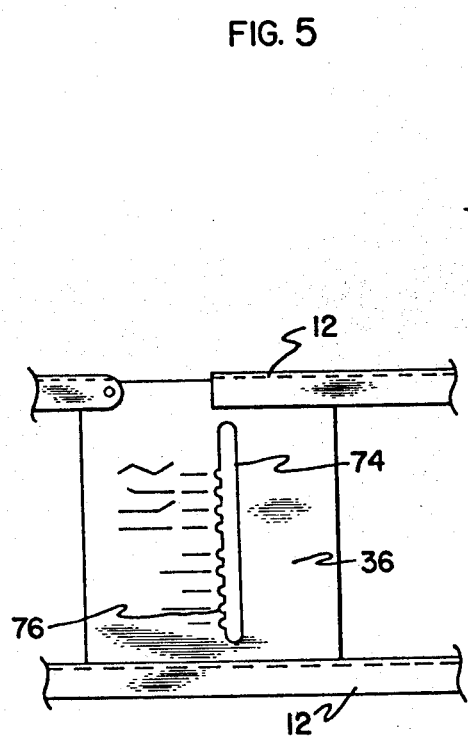
FIG. 7
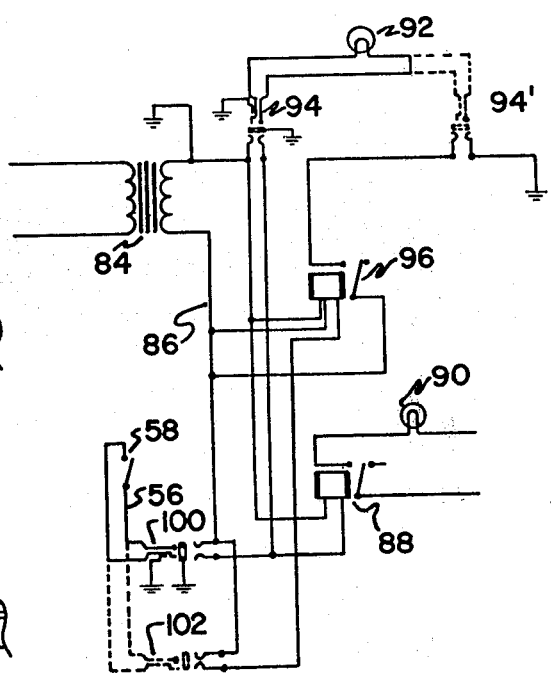
FIG. 8

HEALTH CARE SIGNALING DEVICE

BACKGROUND OF THE INVENTION

In general, the present invention relates to a signaling device and more specifically relates to a signaling device for use in relation to and connected with a hospital, convalescent or other bed wherein the occupant of such bed requires special, continuous care and observation.

The acute shortage of hospital personnel is a matter of common knowledge. Devices which can help to alleviate this shortage of personnel and result in a lowering of the cost of hospital and convalescent care are in great demand. The need for a device capable of monitoring a patient's activity or inactivity which can be installed and incorporated within existing hospital and convalescent home equipment has long been recognized.

The prior art has, on numerous occasions over a long period of time, attempted to deal with the problem of monitoring a patient in bed for a variety of purposes, as indicated by the following patents, and has attempted to deal specifically with the problem of determining a patient's presence or absence from the bed. For example, see U.S. Pat. Nos. 884,121; 1,969,554; 2,260,715; 3,163,856 and 3,325,799.

The prior art has, in general, either failed to provide the degree of sensitivity and ease of adaption to existing equipment which would lead to its wide scale utilization within the health care industry, or has involved such sophisticated electronic techniques as to justify its use only in the most extraordinary of circumstances. This combination of difficulties arises in part from the economic necessities of the health care industry and thus necessitates that any successful invention which is to be adapted on a wide scale throughout the health care industry must constitute a blend of the needed adaptability together with a sufficient degree of sensitivity and responsiveness to be of such real use to the hospital personnel as to justify the cost of installation and operation.

SUMMARY OF THE INVENTION

Accordingly, it is an object of the present invention to provide a new and highly effective sensing and signaling device which overcomes the combined deficiency of the prior art as described above.

It is a further object of the present invention to provide a device capable not only of monitoring a bed to determine if the patient is in or out of bed, but in addition to provide for the monitoring of the restlessness of the patient within the bed, if desired.

A further object of the present invention is to provide for the operation of slave and auxiliary equipment in response to the state of the conditions sensed by the present invention.

It is, also, an object of the present invention to provide a sensing and signaling device which may be readily and effectively installed on existing hospital and convalescent beds without substantial alteration of the bed or large expenditures of time.

Another object of the present invention is to provide for the adjustment of the sensitivity of the sensing device to account for and compensate for the positioning of the various elements of a typical hospital bed or for the weight and size of the patient utilizing such bed.

Other objects and fuller understanding of the present invention may be had referring to the following description and claims taken in conjunction with the accompanying drawings.

The present invention overcomes the deficiencies of the prior art and achieves its objectives by providing an arrangement of crossed wires with a detection ring which operates a mercury switch in response to movements of the various spring and wire elements associated with the structure of a hospital or convalescent bed.

The crossed wire arrangement of the present invention may prove extraordinary sensitivity to the movements of the person on the bed and an indication of that person's movements on any portion of the bed. The present invention, as will be further hereinafter described, provides for ready and close adjustment of the sensitivity of the sensing device. The circuitry provided in accordance with the present invention allows not only for the sensing and signal indication functions of the present invention, but also provides for the operation of slave and auxiliary equipment as desired.

The present invention differs from the prior art known to the applicant in its particular structure namely, the crossed wire arrangement described below, for operation of the switch. The present invention provides far more than a mere switch responsive to the movement of a single spring or element within the bed, but rather provides in a true sense for an integration of the effects of the movement or position of a body on the spring structure of the bed as well as for the detection individual movements on and affecting the springs or wires of the bed's structure. The present invention is particularly adapted to remain fully operative and effective regardless of the positioning of the various elements of the typical hospital bed for the purpose of variously positioning the patient and in each case retains its full sensitivity and responsiveness so as to indicate the conditions desired. The results obtained by the present invention are thus those long desired and recognized in the prior art, but which have heretofore not been successfully incorporated in a single economically feasible unit so as to gain wide acceptance and use throughout the health care industry.

The signaling device of the present invention can alert the nurses' station of the patients needs without the patients conscious effort and is thus invaluable to the occupant of the bed if he is in need of further sedation or cannot or should not leave the bed. Its applicability and use in the monitoring of persons under sedation, the influence of drugs or of any deranged person or of persons restricted in their movements is apparent. In addition the present invention can act not only as a sensing and signaling device per se, but can act to switch on such things as the bathroom light when the occupant of the bed arises or may be utilized to trigger any device electrically actuated such as a T.V. camera, a cardiac monitoring machine and sundry other equipment. Heretofore, so far as the applicant has been able to determine, no effective signaling device has been provided in any but the most extraordinary of circumstances for patients who are restless or coming out of sedation and who thus may be in need of further medication. Without visual observation, the present invention provides such a device which may be utilized with the existing beds, springs and mattresses. Thus, in summary, the present invention provides an inexpensive, economically feasible and effective monitoring system for health care services.

BRIEF DESCRIPTION OF THE DRAWINGS

In order to facilitate the understanding of the present invention, reference will now be made to the appended drawings of a preferred embodiment of the present invention. The drawings should not be construed as limiting the invention, but are exemplary only.

In the drawings:

FIG. 3 is a side view showing the adjustments of the present switch units with an X-ray view of the switch cartridge in its various positions relative to an unoccupied bed.

FIG. 4 is a cross-sectional representation showing the cartridge switch in its "on and off" positions.

FIG. 5 is a cross-sectional representation of an adjustment knob with locking device in accordance with the present invention.

FIG. 6 is a metal plate with ball-bearing adjustment latch in accordance with the present invention.

FIG. 7 is a representation of the complete adjustment plate with the adjustment slot positional knotches according to the configuration of the bed and weight of the individual.

FIG. 8 is a schematic circuit diagram showing the operation of the switch and relay components in accordance with the present invention.

DESCRIPTION OF THE PREFERRED EMBODIMENTS

Figure 1:
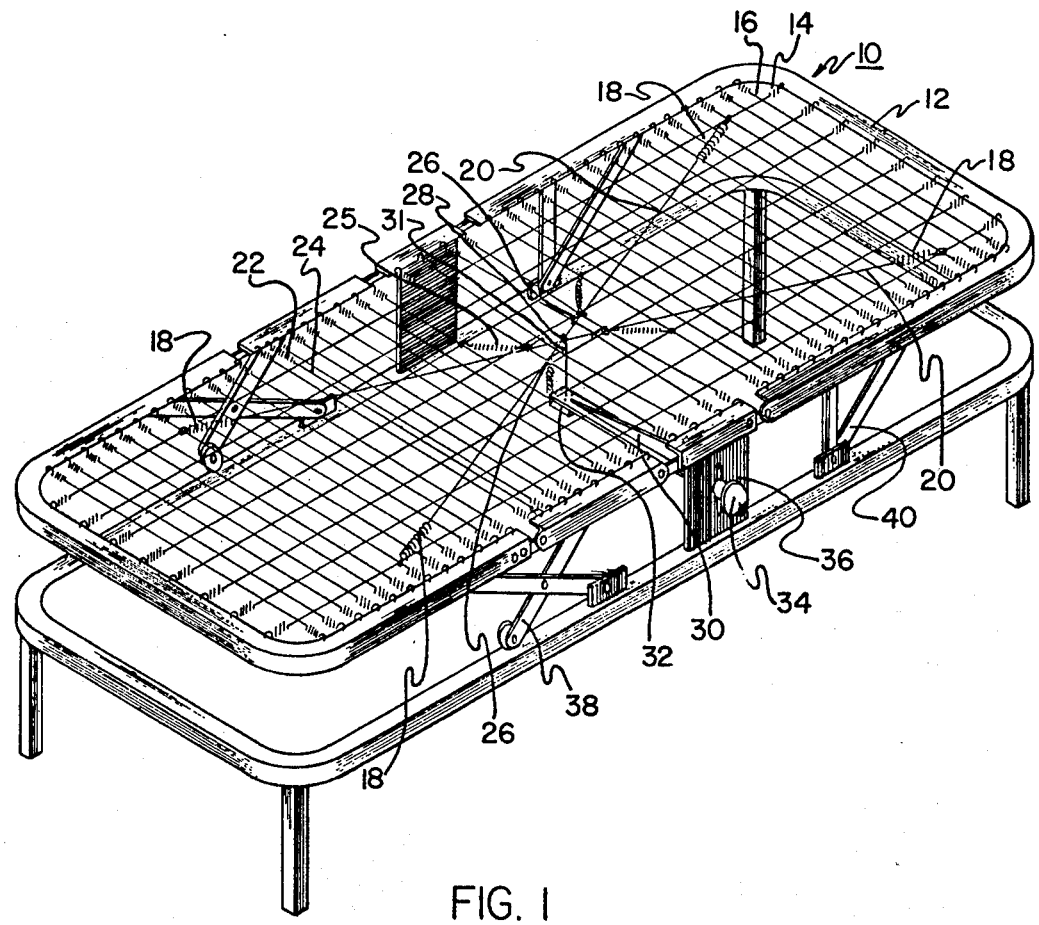
FIG. 1 is a perspective view of a conventional hospital bed without mattress in which the present invention has been incorporated.

A preferred embodiment of the present invention is shown generally in FIG. 1. FIG. 1 illustrates a portion of a typical bed 10 of the type commonly used in hospitals including a frame 12 to which typically are attached springs 14 and wires 16 attached, as shown, around the perimeter of frame 12. As shown the coil springs 18 of the present invention are typically attached to the outermost side strands and typically less than 1/10th of the way down from the head end of the bed and approximately 20% of the distance from the lower or foot end of the bed. These springs are connected to crossed wires 20 as shown in accordance with the present invention. A horizontally mounted coil spring 22 and wire 24 may typically be placed approximately 40% of the distance from the lower end of the bed and preferably in the region of the "knee adjustment" of the bed. The central transverse wires of the bed's structure are held together and remote from the sensing elements by means of clamps 26 and springs 25. Clamps 26 and springs 25 space the transverse wire elements of the bed 16 so as to allow the invention to continue to function with unimpaired sensitivity when the bed is adjusted to a head raised position or other similar typical adjustment positions other than the level position. The crossed wires 20 pass through a non-conductive detection ring 28 which is connected to the switch cartridge 46 by fiber 30. The crossed wires 20 and wire 24 may be moved up and down in accord with the movements of switch support arm 30 which holds the switch cartridge 46 in a switch casing housing 32. A locking adjustment knob 34 mounted within indicator plate 36 mounted on one side of the bed provides for the ease in adjusting to the various bed positions and weight conditions for the patient for whom the bed is made up, without readjustment of the switch cartridge 46.

The crossed wires 20 may be attached further to the bed structure, as necessary depending upon the particular bed, at certain positions such as just above the knee position at the intersection with detection wire 24. Crossed wires 20 maybe attached to the spring wires 16 by means of metal rings to allow for further variations in the adjustment of positions of the bed without altering the sensitivity or effectiveness of the sensing device contained within the switch casing 32. Adjustment means for the bed per se, such as shown at 38 and 40 are intended as representatives of conventional hospital bed adjustment and positioning means and are not a part of the present invention.

Figure 2:
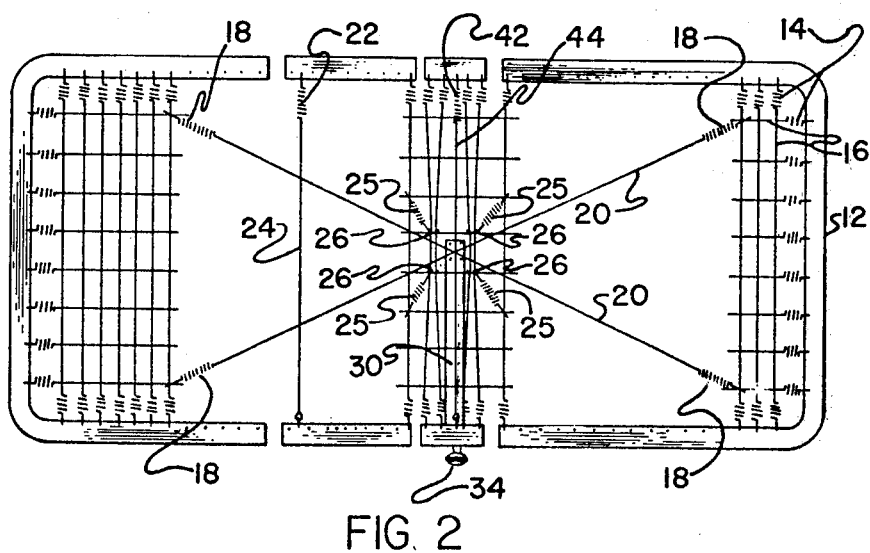
FIG. 2 is a fragmentary top view showing a portion of the wires and springs of a conventional hospital bed in relation to the present invention.

FIG. 2 further illustrates the arrangement of the elements of the present invention within the structure of the spring system of a conventional hospital bed. As noted above, within the frame 12, the hospital bed typically consists of an array of springs 14 and wires 16 connected around the periphery and passing longitudinally and transversely across the bed. As noted above in accordance with the present invention spring means at each end of crossed wires 20 connect to the outermost longitudinal wires 16 at positions of less than 10% of the distance of the length of the total bed from the top portion of the bed and at a position approximately 20% of the total length of the bed above the bottom end of the bed. In the region of the bed adjacent to the break point for knee adjustment an additional control wire 24 is fastened directly on one side to frame 12 and through a spring means 22 to the other side of frame 12. In a like manner in the central position, passing through the non-conductive detection ring 32, may also pass an additional control wire 44 fastened directly to the frame 12 at one side and to the frame 12 at the other side through a spring means 42. The transverse wires immediately adjacent this central portion of the bed may typically be clamped together by a simple clamp means 26 and spring means 25 to prevent their interference with the proper operation of the unit upon raising the upper portion of the bed or upon making other adjustments in the bed's positions and to insure maintenance of proper sensitivity. Also, as noted above, control wire 24 and/or wires 20 may be additionally attached and secured to other transverse or longitudinal spring members to insure proper positioning of the wires as the bed is moved into different and varying positions. In general, however, additional attachments other than those shown are not necessary because of the unique positioning and tensioning of the elements of the present invention which insures that the crossed wires and additional control wires follow the movements of the bed in any position to allow for full sensitivity and effective operation regardless of the positioning of the various elements of the hospital bed.

As shown in FIG. 1 and 2, adjustment knob 34 may be used to adjust within the slot 74 in plate 36 to position the switch positioning arm 30 vertically to allow for various adjustment insensitivity as will be hereinafter described, and for various positionings of switch casing 32 with respect to detection ring 28 and actuating fiber 31. The back of plate 36 may be coated with synthetic resin polymers such as Teflon, nylon and the like to insure ease of adjustment.

As shown in FIG. 3 switch support arm 30 may be moved by the adjustment of adjustment knob 34 to positions as indicated by 30', 34' and 32'. Switch housing 32 contains a suitable switch means such as a mercury switch cartridge 46 which is pivotably mounted within housing 32. The raising and lowering of switch support arm 30 has the effect of adjusting the mercury position within the switch cartridge 46 and thus the sensitivity of the switch in response to the control wire 31 connected to the detection ring 28 through which the crossed wires 20 shown in FIGS. 1 and 2 as well as control wire 44 pass.

As shown in further detail in FIG. 4, as the switch support arm 30 is adjusted up and down to alter the sensitivity of switch cartridge 46, the switch housing 32 connected by fastening means 52 to support arm 30 is also raised and lowered. A control wire 31 of fixed length passes through opening 54 in the housing 32 and attaches by a screw adjustment means 60 to the outer portion of the mercury switch cartridge 46 which is pivotably supported at 48 within the housing 32. Input signal wires 56 pass from the switch electrodes 58 out of housing 32 and interconnect as discussed hereinafter. The positioning of the switch cartridge 46 to the position 46' by virtue of its pivoting about pivot point 48 results in an alteration of position of the mercury 50 within the switch cartridge 46, thereby altering the degree of movement of wire 31 in response to movements transmitted to it through the detection ring 28 by wires 44 or crossed wires 20 so as to result in the completion of the circuit by mercury contact.

As shown in FIG. 5 the adjustment knob 34 may contain a locking mechanism 62 to be opened by a key 64 and retained by a set screw 66 and the action of a differentially threaded screw means 68 which connects with a differentially threaded screw shaft 70 to prevent alteration of the sensing elements even on removal of the locking element shaft 70 has a flattened portion 62 coinciding with the dimensions of slot 74 and ball bearing mechanism 78 engageable with notches 76 along the length of slot 74. The remaining portion of screw shaft 70 is transformed to a cylindrical cross section in region 80 as it passes through the back side of the slot and into a retaining cap 82.

As shown in FIG. 6 when the adjustment knob 34 is unlocked and adjusted to allow free movement the shaft 72 within slot 74, the ball-bearing retaining means 78 may be adjusted from position to position positively engaging notches 76 to bring about the desired adjustment sensitivity in accordance with the height, weight, or position indicated on selection plate 36.

As shown in FIG. 7 the position and sensitivity indicator plate 36 is positioned between the vertical frame structure of a typical hospital bed and has slot 74 in which shaft 72 with the ball-bearing retaining device 78 may be vertically adjusted by adjustment of the actuation knob 34 to a wide variety of positions such as illustrated in FIG. 7. The uppermost position represents the bed with the head raised and the knees flexed. Below that is represented the position for the adjustment of the bed with the feed raised. Represented below that is a position with the head raised or knees flexed and below that a level position. Represented below are adjustments for various weight sensitivities such as, for example, 75, 100, 125, 150, 175 and 200 pound sensitivity positions.

FIG. 8 illustrates a typical control and supervision circuit arrangement utilizing the present invention. Power supplied through transformer 84 is applied through the connecting wires 86 to the mercury switch elements 58 through lead wires 56 as shown in FIG. 4.

When it is desired that the system be utilized for detection of the in or out of bed status of the patient the completion of the circuit by the closing of the mercury switch 58 then provides a completed circuit and power to operate relay 88 and typical slave equipment 90 such as a bathroom light, a room light, a television camera, or other electronic or electrically controlled monitoring apparatus and simultaneously applies power to actuate an indicator lamp 92 at a nurses' control station or other monitoring point when the appropriate telephone style jacks 94 are inserted.

In the event that it is desired to use the system to monitor restlessness of the patient as indicated by the dotted line portions of the drawings, it is arranged in the illustrated circuitry so that the closing of mercury switch elements 58 by virtue of being plugged into a different set of circuitry operate a time delay relay 96 having typically a 30 second hold following the initial triggering action which then serves to retain the monitoring light 92 illuminated for that period of time.

It is believed clear that additional time delay relays may be provided in the circuitry well within the skill of the ordinary artesian to retain certain of the slave equipment such as a television monitor or room lights for a period after return of the patient to bed, or to provide different time sequences than those indicated above. In addition, operation of slave equipment, such as lights and monitoring equipment, may be operated off of the circuitry for detection of restlessness by modification of the circuitry in accordance with that indicated for the in and out of bed portions of the circuitry. Such circuitry may be connected to monitoring and control panels having a multiplicity of various colored lights indicating the status of the patient, the degree of the attention required and similar items. It is also possible that separate indicator lights may be provided for the indication of both restlessness and the condition of being in or out of bed.

In the above discussed preferred embodiments any suitable material of construction may be employed. Typically, the wires referred to are relatively fine steel wire materials of the type of piano wires. Detection ring 28 may be made of any non-conductive material such as Teflon and typically nylon line has been used for element 31. It is believed clear that any other suitable materials may be employed and that the present invention is not necessarily limited to the use of a mercury switch but other suitable position sensitive switches may be employed.

In operation, springs 18 and crossed wires 20 as well as transverse wires 24 and 44 with their respective spring members are attached to the under-structure of the spring array of a typical hospital bed frame 12. The wires 20 and 44 as indicated by the drawings pass through non-conductive detection ring 28 which is connected by a suitable control filament wire 31 to the adjustable switch connecting element 60. A suitably shaped template may be employed to bring the switch to a level position and make any necessary adjustments in length of the control filament 31. The switch support arm 30 may then be set for a specific bed position and patient size. Having made the appropriate adjustment levels for the conditions involved further adjustments may be made merely by altering the position of adjustment knob 34 to the appropriate positions indicated on plate 36.

It has been found as a result of extensive study that in order to turn over in bed it is necessary for one to raise the central portion of the body. The condition of the circuitry illustrated in FIG. 8 is such that when the body weight is present in the bed no light is presented at the monitoring station. In the in and out of bed indication position provided by telephonetype plug 100, the no light indication continues at the monitoring station until the weight on the bed is removed by the person leaving the bed at which time the combined action of detection wires 24, 44 and crossed wires 20 moves the detection ring 28 so as to actuate and effectively move the filamentary connecting wire 31 to pivot mercury switch 46 about point 48 and cause the closing of the connection of mercury switch elements 58, thus producing the resulting transmission of a signal via wires 56 to actuate relays 88 triggering the slave and auxiliary equipment such as lamps, T. V. monitors, charts, graphs, and similar monitoring equipment, and to illuminate light 92 at the monitoring station to indicate that the patient has left the bed.

In the case where it is desired to detect the restlessness of the patient the adjustment knob 34 is adjusted to the patients weight so that the cartridge is at such a level that the slightest movement would cause the circuit to close by closing of the mercury switch elements 58 causing the circuit to pass by means of plug 102 to the time delay relay 96 thereby actuating the holding for a specified period of time through plug 94' the appropriate indicator light 92, such closing of the switch being caused again by the action of wires 24, 44 and crossed wire 20 through detection ring 28 and filamentary connecting element 31, pivoting the mercury switch 46 about point 48 within the switch housing 32.

It is believed clear from the above that a wide variety of material and constructions substitutions may be employed as well as a wide variety of electrical circuit conditions such as voltages, ampherages may be varied in accordance with the needs of the specific institution employing the device. It is further believed clear from the above description that the device and structure of the present invention may be employed to monitor a large number of patients in hospital or convalescent home environment, to monitor the actions and restlessness of the drug addicts, people under sedation, or mentally deranged. It may be used also merely to detect restlessness, to determine when medication is required, to determine patterns of sleep, to determine when individuals are coming out of anesthetic, to monitor a child's bed. The signal thereby produced may be used to turn on a variety of lights, actuate a number of monitoring signal indicators, to turn on cameras, television monitors, recording devices, charts and graphing devices.

The above described circuity which may, for example, typically be operated at 1.5 amperes and 24 volts embodies many important safety features. For example, it has been found that deliberately contacting the lead wires to the spring structure of the bed presents insufficient potential, typically less than 5 volts, to cause a shock or electrical injury in the absense of a good earth ground, such as would not be readily accidentially available in a hospital environment.

It further should be clearly understood that while a specific preferred embodiment of the present invention has been disclosed herein the obvious, analogous substitution of various elements such as black light, ultraviolet light, laser light beams, or simply well collimated light beams anywhere in the physical spectrum may be used in conjunction with a variety of aperture means and photo-sensitive elements in a manner directly analogous to the present invention.

Each of the motion detection wires of the present invention may be replaced by a combination of a light source and photo-sensitive element so as to provide a signal or multiplicity or signals in response to a predetermined deflection of the light beam. Other such variations will be readily apparent to those skilled in the art. Further the responses of such means as disclosed in the present invention in a mechanical form or in the obvious forms of various radiation means may be arranged so as to provide a linear response to the motion transmitted to the switch or may be so arranged as to provide expodential or logarithmic responses to such movements within the bed.

In summary the preferred embodiment as described above operates by the movement of a group of specially positioned control wires 20, etc. responsive to the pressure produced by an occupant in bed. These pressures are transmitted to a single detection ring 28 by the movement and displacement of the control wires 20, etc., causing a displacement of detection ring 28 and the attached filamentary control element 31 so as to pivotably move mercury switch 46 closing and completing circuits to operate slave and auxiliary monitoring equipment and to provide a signal indication of the presence or absence of the occupant of the bed from the bed or through time delay relays of his state of restlessness.

The present invention as described above provides a method of detecting the restlessness or absence of the occupant of a bed by providing an element, as described above, deflectable in response to the movement on the bed and for the detection of the deflection of such elements by completing an electrical circuit in response to the detection of such deflections, thereby providing an audio-visual signal responsive to the completion of such an electrical signal.

Although a specific preferred embodiment of the present invention has been described in detail in the description above, the description is not intended to limit the invention to the particular form or embodiments disclosed herein since they will be recognized as illustrative rather than restrictive. It will be obvious to those skilled in the art that the present invention is not so limited as described in the present specification. The invention is declared to cover all changes and modifications of the specific example of the invention and embodiments disclosed herein for purposes of illustration which do not constitute departures from the spirit and scope of the invention.

What is claimed is:

1. A signaling device for health care to indicate when the occupant of a bed is restless or out of bed comprising at least two spring supported crossed wire elements having the configuration of an X attached to the springs of a hospital bed and at least one control detection wire transverse to said bed and positioned so as to contact said crossed detection wires; said crossed detection wires passing at their point of intersection through a detection element attached by non-conductive filamentary means to a pivotably mounted mercury switch; means for producing a signal indicative of the lack of pressure upon said detection element by the occupant of the bed thereby indicating the occupants absence from the bed or restlessness.

2. The apparatus of claim 1 further requiring that said transverse detection wire pass through the point of intersection of said X configuration control wires.

3. The apparatus of claim 2 whrein in addition to said centrally positioned transverse control detection element said apparatus includes a further detection element between the point of intersection of said X shaped control wires and their terminance at the end closest to a foot of the bed.

4. The apparatus of claim 3 wherein said pivotably mounted switch is mounted at the end of an adjustable cantilevered support arm which may be adjusted to a variety of positions corresponding to various configurations of the hospital bed and patient weights.

5. The apparatus of claim 4 wherein a spring actuated ball-bearing means provides for fixation of said adjustable support arm.

6. The apparatus of claim 5 wherein completion of the circuit by the closing of said mercury switch results in the actuation of slave and auxiliary equipment and a monitoring indicator light indicating the occupants absence from the bed.

7. The invention of claim 5 wherein the closing of the switch actuates a time delay relay producing a continuous lamp signal for a specified period of time indicative of the restlessness of the occupant of the bed.

8. A health care device to indicate when the occupant of a bed is restless or out of bed comprising at least two deflection detecting means operatively connected to the springs of a hospital bed and mounted below the spring structure of said bed in a crossed, X configuration and including at least one control detection means transverse to said bed and positioned so as to operatively cooperate with said crossed, X configuration of deflection detecting means, said deflection detecting means being deflectable in response to movement on said bed for detecting said movement and crossing at their point of intersection through a detection and circuit completing means responsive to said deflection detecting means for producing a signal indicative of said movement on said bed.

* * * * *